(12) United States Patent
Pacheco et al.

(10) Patent No.: US 9,364,275 B2
(45) Date of Patent: Jun. 14, 2016

(54) COMPRESSION INSTRUMENT

(71) Applicant: Stryker Trauma AG, Selzach (CH)

(72) Inventors: Fernando Ferreira Monteiro Pacheco, Zürich (CH); Guillaume Bugnard, Bern (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 170 days.

(21) Appl. No.: 14/073,219

(22) Filed: Nov. 6, 2013

(65) Prior Publication Data

US 2014/0128926 A1    May 8, 2014

(30) Foreign Application Priority Data

Nov. 7, 2012   (EP) .................................. 12 191 599

(51) Int. Cl.
*A61B 17/86* (2006.01)
*A61B 17/88* (2006.01)
*A61B 17/84* (2006.01)

(52) U.S. Cl.
CPC .............. *A61B 17/864* (2013.01); *A61B 17/863* (2013.01); *A61B 17/8875* (2013.01); *A61B 17/8891* (2013.01); *A61B 17/848* (2013.01)

(58) Field of Classification Search
CPC . A61B 17/17; A61B 17/8875; A61B 17/8891
See application file for complete search history.

(56) References Cited

U.S. PATENT DOCUMENTS

| 4,463,753 | A | 8/1984 | Gustilo | |
|---|---|---|---|---|
| 8,992,587 | B2 * | 3/2015 | Kirschman | ................... 606/305 |
| 2003/0083667 | A1 * | 5/2003 | Ralph et al. | ..................... 606/96 |
| 2009/0228053 | A1 | 9/2009 | Kolb et al. | |

FOREIGN PATENT DOCUMENTS

| DE | 29710979 U1 | 8/1997 |
|---|---|---|
| DE | 102009033138 A1 | 2/2011 |
| WO | 2006047581 A2 | 5/2006 |
| WO | 2009134888 A2 | 11/2009 |
| WO | 2009134893 A2 | 11/2009 |
| WO | 2009134896 A2 | 11/2009 |

OTHER PUBLICATIONS

U.S. Appl. No. 13/589,593, filed Aug. 20, 2012.
Reduction Instruments 2009.
Extended European Search Report for Application No. 12191599.5 dated Feb. 18, 2013.

* cited by examiner

*Primary Examiner* — Andrew Yang
(74) *Attorney, Agent, or Firm* — Lerner, David, Littenberg, Krumholz & Mentlik, LLP (57) ABSTRACT

A system and method for pressing fragments of a fracture against each other includes a compression device comprising a hollow shaft. The system has an inner engagement portion for engaging an outer feature of a screw head arranged at a distal end of the shaft. The system has a supporting element with a contact surface adapted to abut on one of the fragments, and a joint is provided between the supporting element and the hollow shaft. The joint is formed so as to allow a rotation of the shaft about a longitudinal axis thereof relative to the supporting element. Additionally, the joint is formed to allow a pivot movement of the supporting element relative to the shaft.

20 Claims, 6 Drawing Sheets

COMPRESSION INSTRUMENT

CROSS-REFERENCE TO RELATED APPLICATIONS

The present application claims priority from European Patent Application 12 191 599.5 filed on Nov. 7, 2012, the disclosure of which is hereby incorporated herein by reference.

BACKGROUND OF THE INVENTION

The present application claims priority from European Patent Application 12 191 599.5 filed on Nov. 7, 2012, the disclosure of which is hereby incorporated herein by reference.

The invention relates to a device for fracture reduction and/or intrafragmentary compression. Furthermore, the invention relates to a method for operating the device. Compression screws may be introduced into a fractured object (bone) by means of a compression device adapted to press fragments of the object against each other. Usually, the longitudinal axis of the elongated compression device extends along the longitudinal axis of the compression screw so that the screw may be rotated by rotating the compression device about that axis.

However, the contact surface, i.e. the end face of the compression device, which has to come in contact with the fractured object for applying a force which presses fragments of the fractured object against each other, will cause undesired damage or injury to the contact area adjacent the entry point of the compression screw at the object. This may particularly be caused due to the rotation of the compression device creating friction, as well as due to an uneven or inclined abutment of the end face of the compression device onto the object surface.

BRIEF SUMMARY OF THE INVENTION

One aspect of the invention may be to provide a device and a method for pressing two fragments of a fracture against each other, with a reduced interference between the device and the fragments. Another aspect may be to provide a device and a method by means of which fragments of a fracture can be stably and reliably pressed against each other.

This is achieved by the subject-matter of the respective independent claims. Further embodiments are described in the dependent claims.

In general, a system for pressing fragments of a fracture against each other according to an embodiment, includes a compression device comprising a hollow shaft, wherein an inner engagement portion for engaging an outer feature of a screw head is arranged at a distal end of the shaft, a supporting element with a contact surface adapted to abut on one of the fragments, and a joint between the supporting element and the hollow shaft. The joint is formed so as to allow a rotation of the shaft about a longitudinal axis thereof relative to the supporting element. Additionally, the joint is formed to allow a pivot movement of the supporting element relative to the shaft.

It is noted that the rotation may be realized like a shaft bearing with or without rolling elements. On the other hand, the pivot movement may be realized about only one axis but also about two or more axes, such as a ball and socket joint.

According to one embodiment, the joint may include a ball joint, wherein the joint may include an outer spherical portion formed at the distal end of the hollow shaft, and an inner spherical portion formed at the supporting element. It will be understood that the outer spherical portion, i.e. a part of a ball, may be formed at the supporting element, whereas the inner spherical portion may be formed at the distal end of the hollow shaft.

According to another embodiment, the joint between the hollow shaft and the supporting element includes a snap fit connection which may provide for the possibility to separate the supporting element from the hollow shaft. Accordingly, it may be possible to utilize a single supporting element together with a plurality of different hollow shafts, as long as the respective hollow shaft is provided with a joint element which corresponds to the counterpart at the supporting element.

The provision of a joint between the supporting element and the hollow shaft allows a flat and smooth abutment of the contact surface at the supporting element on an outer surface of a fragment, even if it is intended to introduce a compression screw into the fragment with a non-perpendicular angle, i.e. inclined, between the longitudinal axis of the screw (the hollow shaft) and the outer surface of the fragment, adjacent the entry point of the screw into the fragment.

Regarding the inner engagement portion for engaging an outer feature of a screw head, it is noted that any contour may be suitable as long as it comprises at least one edge on the circumference which allows applying a rotational force on a screw head. For example, the inner engagement portion may be formed like a hexagonal wrench adapted to fit to a screw head formed like a hexagonal nut.

According to a further embodiment, the inner engagement portion at the distal end of the hollow shaft comprises an inner thread for engaging an outer thread formed on a screw head.

According to yet another embodiment, the system further comprises a compression screw having a first outer thread at a distal end and a proximal end referred to in the following as screw head, with an outer feature corresponding to the inner engagement portion of the hollow shaft. That is, the system may comprise a combination of a compression device and a compression screw, wherein the head of the compression screw fits into the inner engagement portion at the distal end of the shaft of the compression device.

In a case, in which the inner engagement portion comprises a thread, the screw head should have also a corresponding thread.

It is noted that a screw having a first thread on the distal portion of the screw shaft as well as a second thread on the screw head may be screwed completely into an object, with the diameter of the two threads being substantially the same. Even if the diameter of the shaft is smaller than the diameter of the head, it is possible to provide the threads with the same pitch so that both threads may engage simultaneously at an object to be screwed into the same.

According to an embodiment, a pitch of the outer thread at a distal end of the compression screw may be greater than a pitch of an outer thread at the screw head. Such a configuration results primarily in different lengths per turn by which the respective threads enter an object. In a case in which the distal thread engages in a first fragment and the proximal thread engages in a second fragment, these fragments will be pulled together or pushed away from each other depending on the rotation direction of the screw. Accordingly, it is possible to achieve a further compression between two fragments by completely screwing in the compression screw into both fragments.

To allow a controlled introduction of a compression screw into an object, the system may further comprise a drill to prepare a bore for receiving the compression screw.

According to another embodiment, the compression screw further comprises a through bore in a longitudinal direction of the screw, so that the compression screw may be adapted to slide onto a Kirschner wire, with the Kirschner wire accommodated in the through bore of the compression screw.

According to yet a further embodiment, the system may further comprise a screwdriver with an outer screw engagement portion at a distal end of the screwdriver. The screwdriver may be adapted to be at least partially accommodated in the hollow shaft of the compression device. On the other hand, the compression screw may further comprise a corresponding inner tool engagement portion formed in the screw head, for engaging the outer screw engagement portion of the screwdriver.

In general, a method for pressing fragments of a fracture against each other comprises the steps of coupling a screw head of a compression screw with a hollow shaft of a compression devise, rotating and thus screwing in the compression screw by rotating the compression device through a first fragment and into a second fragment, until a contact surface of a supporting element of the compression device abuts on the first fragment, and pressing the first and second fragments against each other by further rotating the compression device and thus the compression screw.

According to an embodiment, the compression screw may be screwed into a bore previously prepared into the first and second fragments for receiving the compression screw.

According to another embodiment, the method may further comprise the steps of coupling an outer screw engagement portion of a screwdriver with an inner tool engagement portion in the screw head of the compression screw, and disconnecting the hollow shaft from the head of the compression screw. Furthermore, the compression screw may be completely screwed into an object by means of the screwdriver, while disconnecting the compression screw from the shaft of the compression device, i.e. while turning the outer thread at the screw head out of the inner thread in the hollow shaft. This is possible with the contact surface of the supporting element being in contact with an outer surface of a fragment.

It has to be noted that embodiments of the invention are described with reference to different subject-matters. In particular, some embodiments are described with reference to method-type claims, whereas other embodiments are described with reference to apparatus-type claims. However, a person skilled in the art will gather from the above and the following description that, unless otherwise notified, in addition to any combination of features belonging to one type of subject-matter, also any combination of features relating to different subject-matters is considered to be disclosed with this application.

These and other objects, features and advantages of the exemplary embodiments of the present invention will become apparent upon reading the following detailed description of exemplary embodiments, when taken in conjunction with the appended claims.

It is noted that the illustration in the drawings is only schematically and not to scale. Throughout the drawings, the same reference numerals and characters, unless otherwise stated, are used to denote like features, elements, components, or portions of the illustrated embodiments. Moreover, while the present invention will now be described in detail with reference to the figures, it is done so in connection with the illustrative embodiments and is not limited by the particular embodiments illustrated in the figures, as defined by the appended claims.

DETAILED DESCRIPTION

Figure 1:
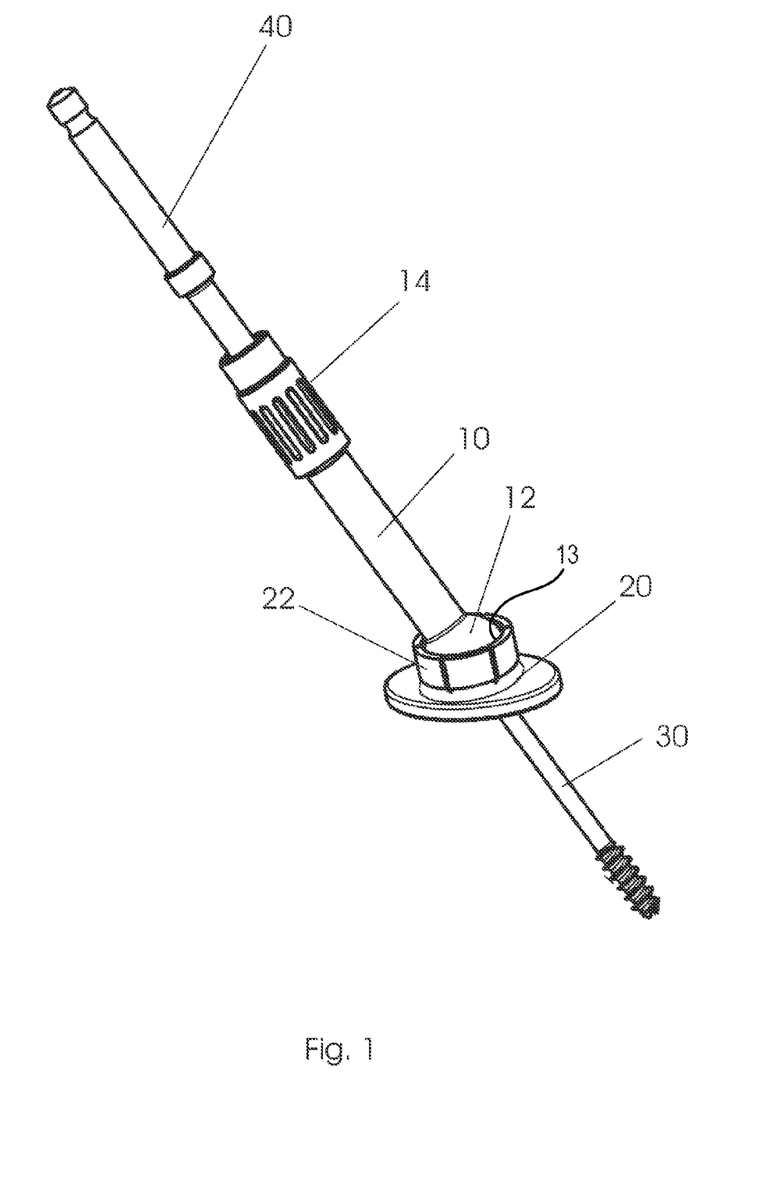
FIG. 1 is an isometric visualization of an embodiment of a system with a compression device, a compression screw and a screwdriver.

FIG. 1 provides an isometric illustration of an embodiment of a system for pressing fragments against each other, the system comprising a compression device, a compression screw 30 and a screwdriver 40. The compression device comprises a hollow shaft 10 and a supporting element 20.

The hollow shaft 10 of the compression device includes a ball head, i.e. an outer spherical surface 12 formed at a distal end of the hollow shaft 10 and a grip portion 14 at a proximal end portion of the hollow shaft. The spherical portion may be formed integrally with or may be attached to the hollow shaft. The grip portion may be formed as a thickened portion onto the sleeve-like shaft with grooves on its circumference allowing a better grip.

Fixed on the spherical portion 12 of the shaft 10 is a supporting element 20 including a portion 22 with an inner spherical recess 13 which corresponds to the outer spherical portion 12 of the hollow shaft 10. The supporting element further comprises a flat plate portion which provides an enlarged contact area in order to distribute the load more evenly on the object surface acting as a temporary washer. Furthermore, with the ball joint the screw may be inserted at an angle other than 90 degrees to the object surface. Lastly, the plate does not rotate with the shaft during the compression process. Thus, friction on the object surface is avoided.

Figure 2:
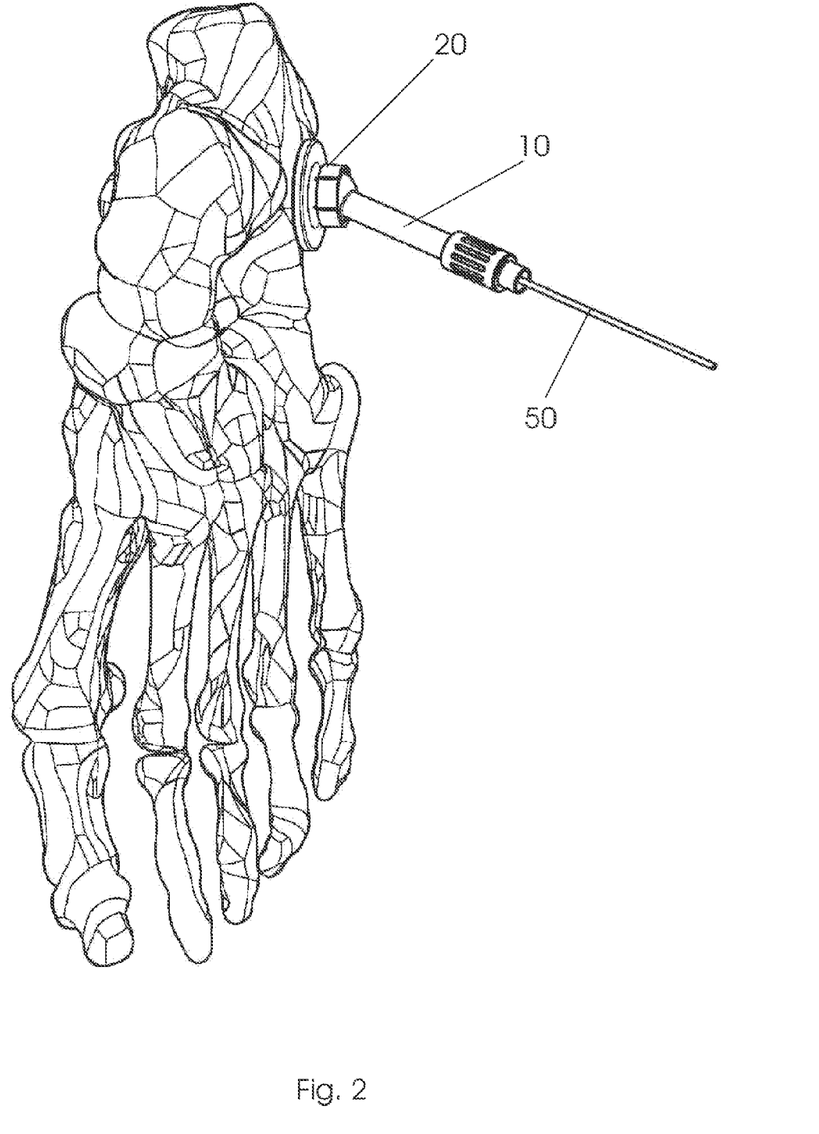
FIG. 2 shows an example of use of the system according to another embodiment.

FIG. 2 shows an example of use of a system according to another embodiment. Here, the system comprises a compression device with a hollow shaft 10 and a supporting element 20, as well as a Kirschner wire, i.e. a means for preparing a bore 50 in the fragments and for leading a compression screw along a desired path into the object which is in this case a foot bone. As can be seen, the screw has been inserted with an angle of approximately 60 degrees with respect to the bone surface onto which the contact surface of the supporting element 20 abuts. The ball joint allows both the rotation of the shaft 10 relative to the supporting element 20 and an angled positioning of the supporting element relative to the shaft.

Figure 3:
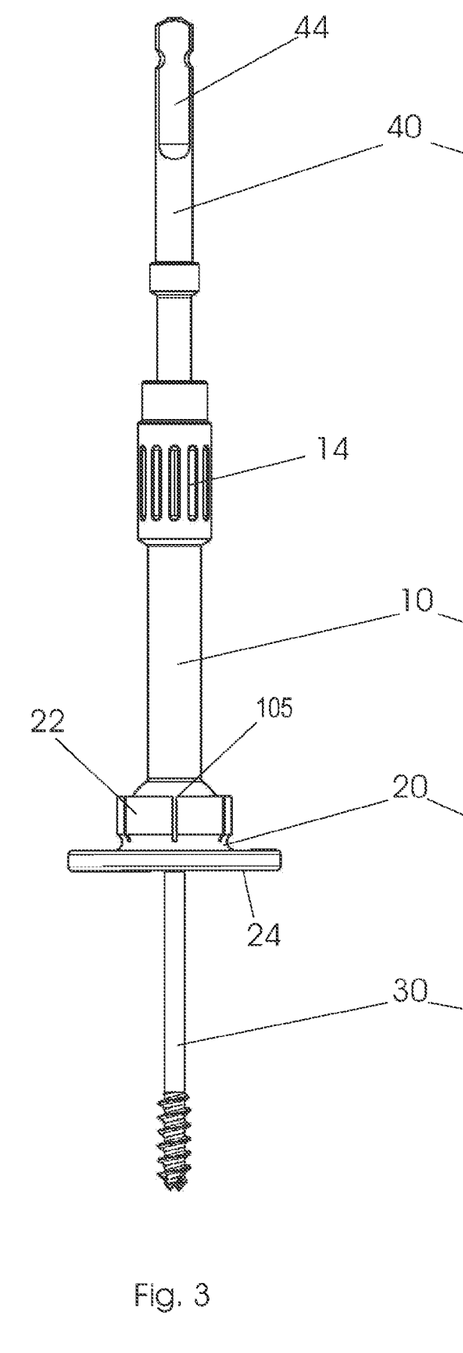
FIG. 3 is a side view of a system according to an embodiment.
Figure 4:
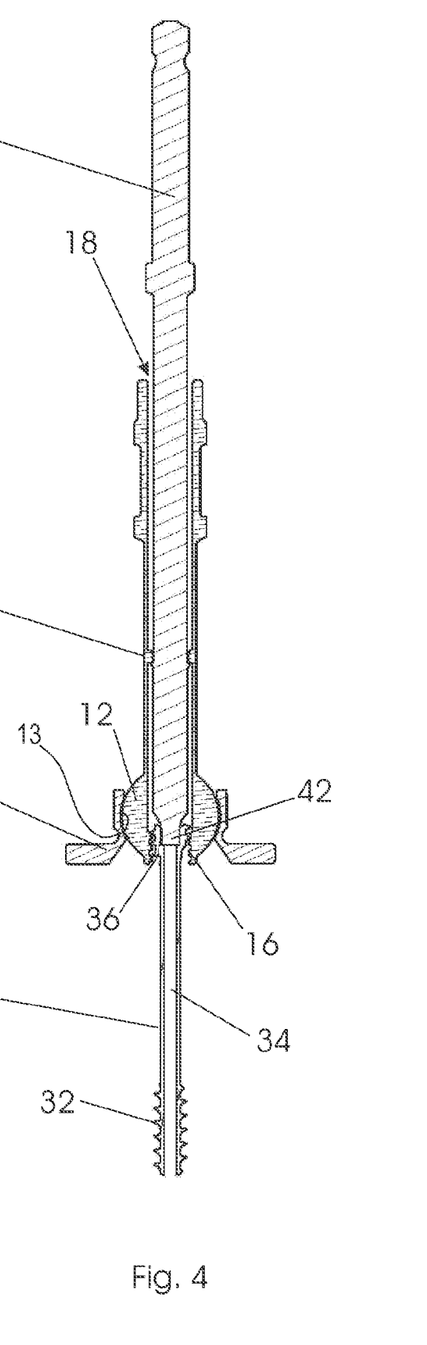
FIG. 4 is a section view of the system of FIG. 3.

FIG. 3 is a side view of a system comprising a compression device with a shaft 10 and a supporting element 20, the system further comprising a compression screw 30 and a screwdriver 40. FIG. 4 is a section view of the system of FIG. 3. FIG. 4 particularly shows the ball joint between the hollow shaft 10 and the supporting element 20. The portion 22 includes an inner spherical portion 13 in which the outer spherical portion 12 is arranged. As shown in FIG. 3, axial slots 105 are provided in the portion 22, wherein these slots provide an elasticity of the respective circumferential sections in a radial direction so that a snap fit is realized between the inner spherical portion of portion 22 and the outer spherical portion 12.

There may be five, six or even more slots 105. The contact surface of the supporting element which is, in this example, arranged perpendicular to the longitudinal axis of the hollow shaft, is denoted with reference sign 24 in FIG. 3.

Denoted with reference sign 18 in FIG. 4 is a through bore 18 formed in the shaft 10 for accommodating for example a screwdriver 40. At the proximal end of the screwdriver, a grip coupling portion 44 may be provided for a form-fit connection between the elongated shaft of the screwdriver and a grip which may have a greater diameter. The compression screw 30 is provided with a through bore 34 through which a Kirschner wire may extend leading the screw to the desired location in for example a bone. At the distal end portion of the compression screw a first outer thread 32 is formed.

Figure 5:
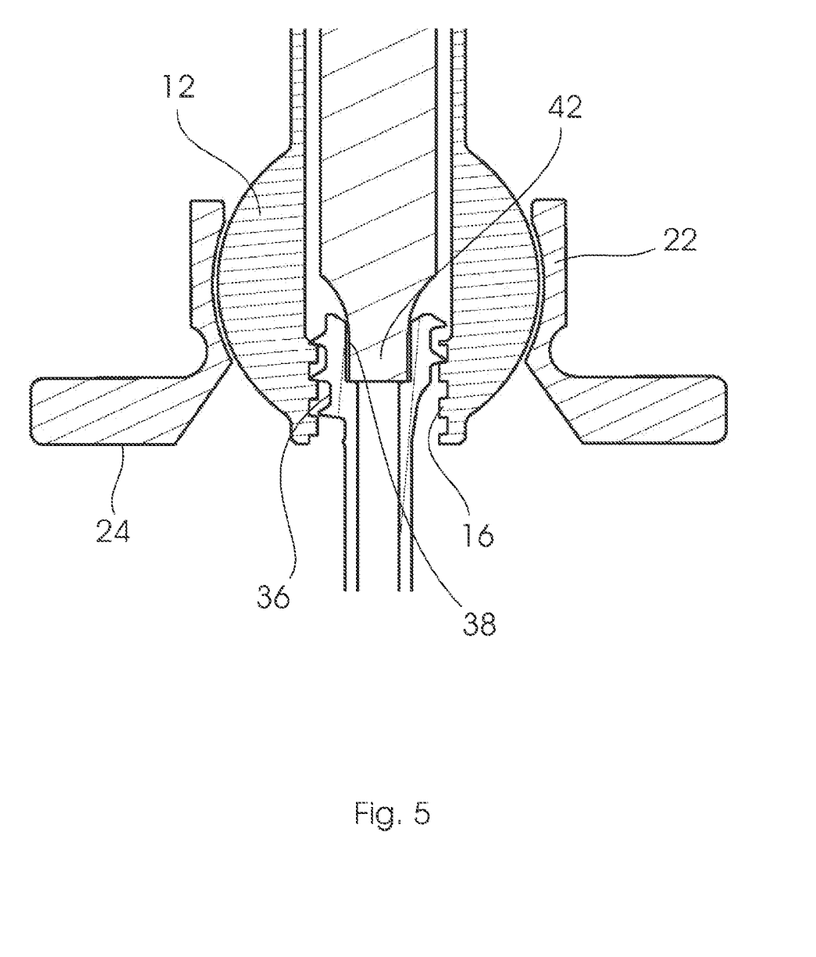
FIG. 5 is a detail view of a joint between a supporting element and a hollow shaft.

The section including the ball joint is further detailed in FIG. 5. In the shown embodiment, the spherical portion 12 is integrally formed with and at the distal end of the hollow shaft, and an inner engagement portion in form of a thread 16 is formed at the distal end of the through bore inside the shaft. The inner thread 16 engages with an outer thread 36 formed on the outer surface of the head of the compression screw. Furthermore, an inner tool engagement portion 38 is formed in the screw head so that a corresponding outer screw engagement portion 42 of a screwdriver as well as the inner thread 16 of the shaft may engage the screw head at the same time. Therefore, the compression screw may be easily disconnected from the shaft by rotating the shaft and the screwdriver in opposite directions relative to each other.

Figure 6:
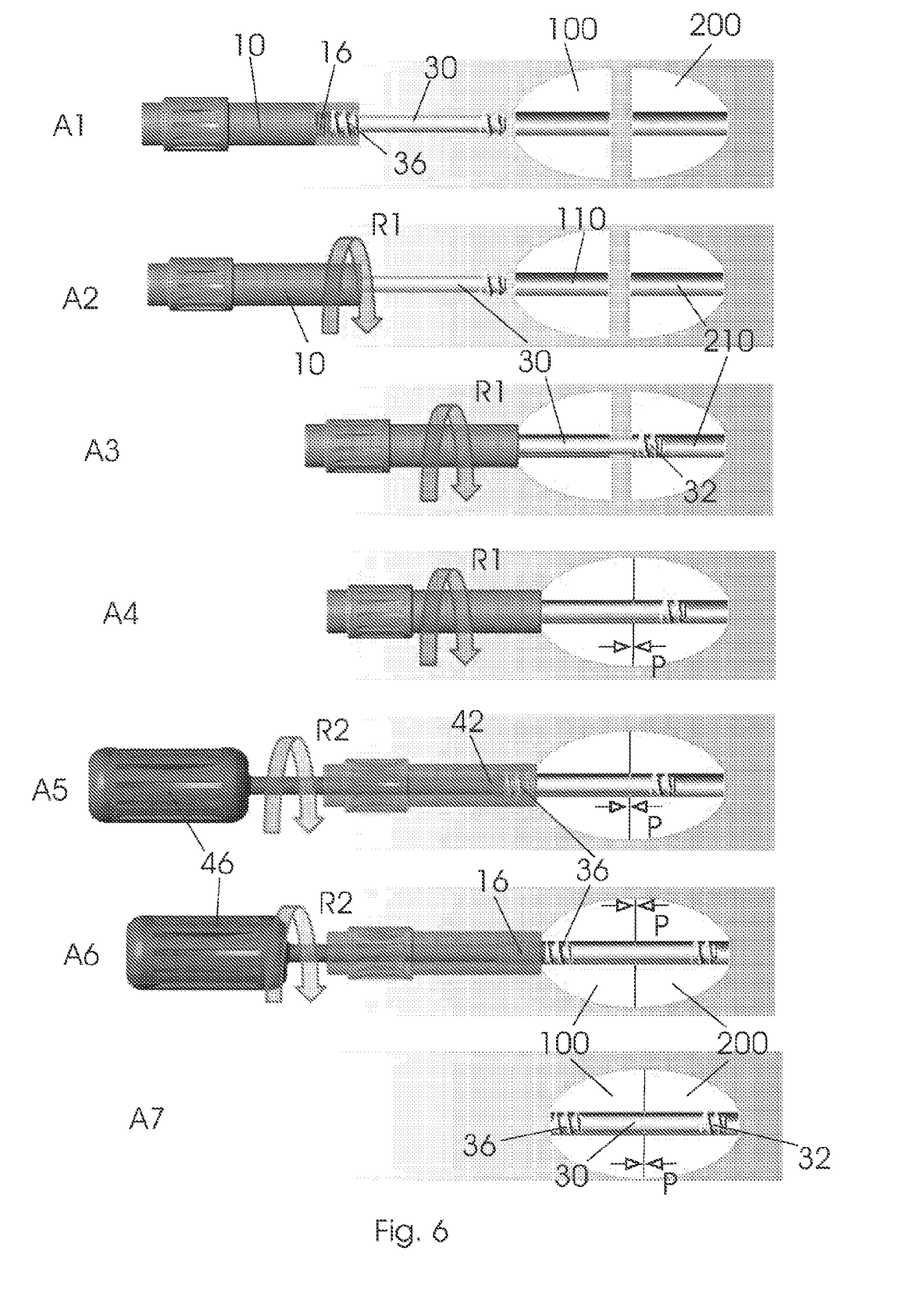
FIG. 6 illustrates steps of a method according to one embodiment.

FIG. 6 shows a series of sketches schematically illustrating a sequence of stages during a process of pressing two fragments against each other. It is noted that for reasons of clear view the supporting element is omitted in the sketches of FIG. 6.

In stage A1, the outer thread 36 at the proximal end of the compression screw 30 is coupled to the inner thread 16 of the hollow shaft 10. Furthermore, the first fragment 100 as well as the second fragment 200, to be pressed together, have been provided with a bore for receiving the compression screw.

In stage A2, the combination of the shaft 10 and the screw 30 is rotated, indicated by arrow R1, so as to be inserted firstly into bore section 110 of fragment 100.

In stage A3, the combination is further rotated so that the distal thread 32 of the screw 30 is inserted into bore section 210 of fragment 200, after leaving the first bore section 110 of fragment 100.

In stage A4, the combination of shaft and screw is further rotated so that the second fragment is pulled towards the first fragment, until the fragments are in contact to each other. In this situation, further rotating of the shaft and screw result in a pressure P acting between the fragments. This can be achieved when no thread of the screw engages the first fragment. Instead, the first fragment should merely be supported by the end face of the shaft, i.e. the contact surface of the supporting element.

In stage A5, a screwdriver having a grip 46, is introduced through the through bore of the hollow shaft until the distal screw engagement portion 42 of the screwdriver engages the inner tool engagement portion in the screw head, with the outer thread 36 at the screw head furtheron engaging the inner thread in the distal end of the hollow shaft. The pressure P is maintained.

In stage A6, the compression screw is further rotated by means of the screwdriver, indicated by arrow R2, while the hollow shaft may be not moved, i.e. may be hold stably. By the rotation of the screwdriver with the screw relative to the shaft, the proximal thread 36 of the compression screw is disconnected from the inner thread 16 of the shaft, and at the same time screwed into the first fragment 100. As soon as the thread 36 is completely inserted into the fragment 100, it is easy to remove the compression device including the shaft as well as the screwdriver.

In stage A7, a fixation of the fragments 100, 200 is achieved. The compression screw 30 is completely inserted into both fragments, with the distal thread 32 engaging the second fragment 200 and the proximal thread 36 engaging the first fragment 100. The pressure P may be increased while the proximal thread 36 has been screwed into the first fragment, in a case in which the pitches of the thread differ from each other, as described above.

Figure 7:
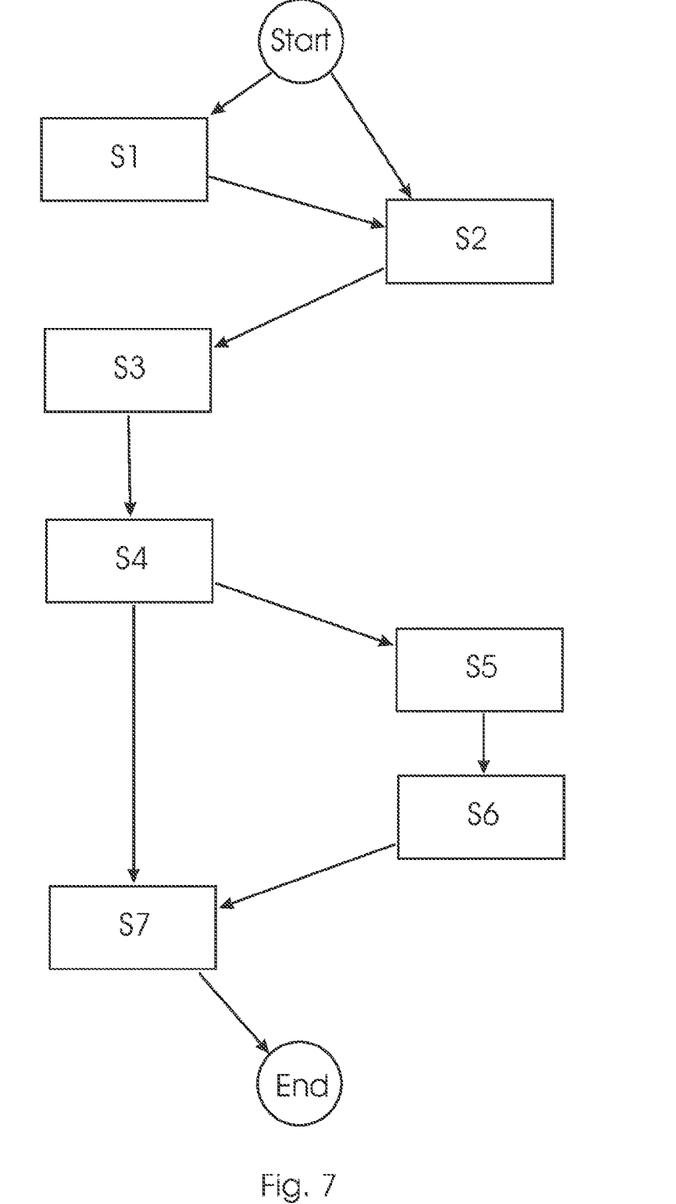
FIG. 7 is a flowchart representing method steps in accordance with embodiments.

The flow-chart in FIG. 7 illustrates the principles of using the system according to slightly different embodiments, i.e. the flow-chart illustrates the principles of operating the system. It will be understood that the described steps are major steps, wherein these major steps might be differentiated or divided into several sub-steps. Furthermore, there might be also sub-steps between these major steps.

The schematically illustrated methods start at the circle denoted with 'start'.

In step S1, a bore is prepared in fragments of a fracture, for receiving a compression screw. Step S1 is an optional step.

In step S2, which may be an initial step or which may follow the step of preparing a bore, an outer engagement portion at a proximal end of a compression screw is coupled with a corresponding inner engagement portion of a rotatable shaft of a compression device.

In step S3, the screw is screwed in and through a first fragment and into a second fragment, by rotating the shaft of the compression device. A result of this step is that the first and second fragments abut on each other and the contact surface of the supporting element abuts on the outer surface of the first fragment.

In step S4, a pressure is build up between the fragments, by further rotating the shaft of the compression device and thus the compression screw, with the first fragment compressed between the contact surface of the supporting element and the second fragment.

In step S5, which may be an optional step, a distal screw engagement portion of a screwdriver is coupled with an inner tool engagement portion at the screw head of the compression screw.

In step S6, particularly the proximal thread of the compression screw is screwed in the first fragment until the compression screw is completely inserted into the fragments. Simultaneously, the proximal thread may be disengaged from the inner thread at the distal end of the shaft of the compression device. In other words, the proximal thread of the compression screw is screwed out of the thread of the shaft and into the first fragment, simultaneously.

It is noted that either at the end of step S4 or at the end of step S6, the intended pressure between the fragments may be achieved.

In step S7, the compression device with the hollow shaft and the supporting element is removed from the compression screw. In the case in which the screw is completely inserted, also the screwdriver is removed from the compression screw.

The methods end at the circle denoted with 'end'.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practising the claimed invention, from a study of the drawings, the disclosure, and the appended claims.

In the claims, the word "comprising" does not exclude other elements, and the indefinite article "a" or "an" does not exclude a plurality.

The mere fact that the certain measures are recited in mutually different dependent claims does not indicate that a combination of these measures cannot be used to advantage. Any reference signs in the claims should not be construed as limiting the scope.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for pressing fragments of a fracture against each other, including a compression device, the system comprising:
a hollow shaft with a longitudinal axis, wherein an inner engagement portion for engaging an outer feature of a screw head is arranged at a distal end of the shaft;
a supporting element with a contact surface adapted to abut on one of the fragments, and
a joint between the supporting element and the hollow shaft;
wherein the joint allows the shaft to be rotatable about the longitudinal axis relative to the supporting element, and the joint allows the supporting element to be pivotable relative to the shaft; and
wherein the inner engagement portion comprises an inner thread for engaging an outer thread formed on the screw head.

2. The system of claim 1, wherein the joint includes a ball joint.

3. The system of claim 1, wherein the joint includes an outer spherical portion formed at the distal end of the hollow shaft, and an inner spherical portion formed at the supporting element.

4. The system of claim 1, wherein the joint includes a snap fit connection.

5. The system of claim 1, the system further comprising a compression screw having a first outer thread at a distal end and a screw head with an outer feature corresponding to the inner engagement portion of the hollow shaft.

6. The system of claim 5, wherein the outer feature at the screw head is a second outer thread.

7. The system of claim 6, wherein a pitch of the first outer thread is greater than a pitch of the second outer thread.

8. The system of claim 5, wherein the compression screw further comprises a through bore in a longitudinal direction of the screw.

9. The system of claim 5, wherein the compression screw further comprises an inner tool engagement portion formed in the screw head, for engaging an outer screw engagement portion of a screwdriver.

10. The system of claim 8, further comprising a Kirschner wire, wherein the compression screw is adapted to slide over the Kirschner wire, with the Kirschner wire accommodated in the through bore of the compression screw.

11. The system of claim 9, further comprising a screwdriver with an outer screw engagement portion at a distal end of the screw driver, the screw driver being adapted to be at least partially accommodated in the hollow shaft.

12. A method for pressing fragments of a fracture against each other, the method comprising the steps of:
coupling a screw head of a compression screw with an inner engagement portion at a distal end of a hollow shaft of a compression devise;
rotating and thus screwing in the compression screw through a first fragment and into a second fragment, until a contact surface of a supporting element of the compression device abuts on the first fragment; and
pressing the first and second fragments against each other by further rotating the compression screw;
coupling an outer screw engagement portion of a screwdriver with an inner tool engagement portion in the screw head of the compression screw; and
disconnecting the hollow shaft from the head of the compression screw.

13. The method of claim 12, further comprising the step of preparing a bore into the first and second fragments for receiving the compression screw.

14. A system for pressing fragments of a fracture against each other comprising:
a compression screw having a cannulated bore therethrough, a first end with a first outer threaded portion and a second end with a second outer threaded portion, the first and second end portions spaced apart by a shaft portion having a non-threaded outer surface;
a guide shaft having a bore therethrough and a first end having a part-spherical outer surface, the guide shaft bore adjacent the first end having an inner threaded portion for threadably receiving at least the second outer threaded portion of the compression screw;
a supporting element having an opening therethrough with a part-spherical inner surface for rotatably receiving the part-spherical outer surface of the guide shaft, the supporting element having a first end with a bore contacting surface; and
a screw driver for extending through the bore in the guide shaft engageable with a drive element formed on the second end of the compression screw.

15. The system of claim 14, wherein a pitch of the first outer thread is greater than a pitch of the second outer thread.

16. The system as set forth in claim 14 wherein the supporting element has a radially expandable portion at a second end thereof, the expandable portion at least partially surrounding the part-spherical inner surface of the supporting element.

17. The system as set forth in claim 16, wherein the radical expandable portion at the second end of the supporting element has a circumferential wall having a plurality of circumferentially spaced slots therein.

18. The system as set forth in claim 14, wherein the inner threaded portion at the first end of the guide shaft threadably receives both the first and second outer threaded portions of the compression screw.

19. A system for pressing fragments of a fracture against each other, including a compression device, the system comprising:

a hollow shaft with a longitudinal axis, wherein an inner engagement portion for engaging an outer feature of a screw head is arranged at a distal end of the shaft;

a supporting element with a contact surface adapted to abut on one of the fragments, and a joint between the supporting element and the hollow shaft;

wherein the joint allows the shaft to be rotatable about the longitudinal axis relative to the supporting element, and the joint allows the supporting element to be pivotable relative to the shaft; and the system further comprising a compression screw having a first outer thread at a distal end and a screw head with an outer feature corresponding to the inner engagement portion of the hollow shaft.

20. The system of claim 19, wherein the outer feature at the screw head is a second outer thread.

\* \* \* \* \*